US012427232B2

(12) United States Patent
Reed et al.

(10) Patent No.: US 12,427,232 B2
(45) Date of Patent: Sep. 30, 2025

(54) BREAST PUMP WITH VIBRATION UNIT AND HEATER

(71) Applicant: Dr. Brown's Company, St. Louis, MO (US)

(72) Inventors: Mark D. Reed, Columbia, IL (US); Rebecca Brandt White, Ballwin, MO (US); Amanda Auger, St. Louis, MO (US)

(73) Assignee: Dr. Brown's Company, St. Louis, MO (US)

( * ) Notice: Subject to any disclaimer, the term of this patent is extended or adjusted under 35 U.S.C. 154(b) by 0 days.

(21) Appl. No.: 18/715,976

(22) PCT Filed: Nov. 8, 2022

(86) PCT No.: PCT/US2022/079462
§ 371 (c)(1),
(2) Date: Jun. 3, 2024

(87) PCT Pub. No.: WO2023/107791
PCT Pub. Date: Jun. 15, 2023

(65) Prior Publication Data
US 2024/0416017 A1 Dec. 19, 2024

Related U.S. Application Data

(60) Provisional application No. 63/286,281, filed on Dec. 6, 2021.

(51) Int. Cl.
*A61M 1/06* (2006.01)
*A61M 1/00* (2006.01)
(52) U.S. Cl.
CPC ............ *A61M 1/066* (2014.02); *A61M 1/067* (2021.05); *A61M 1/80* (2021.05); *A61M 1/069* (2021.05);
(Continued)

(58) Field of Classification Search
CPC ........ A61M 1/066; A61M 1/067; A61M 1/80; A61M 2205/36; A61M 2205/82;
(Continued)

(56) References Cited

U.S. PATENT DOCUMENTS 7,243,616 B2 7/2007 Fei
7,972,297 B2 7/2011 Bryan et al.
(Continued)

FOREIGN PATENT DOCUMENTS

WO 2012037848 A1 3/2012

OTHER PUBLICATIONS

International Search Report and Written Opinion for Patent Application No. PCT/US2022/079462 mailed Feb. 1, 2023; 11 pp.

*Primary Examiner* — Laura A Bouchelle
*Assistant Examiner* — Anna E Goldberg-Richmeier
(74) *Attorney, Agent, or Firm* — Armstrong Teasdale LLP

(57) ABSTRACT

A breast pump includes a housing including a first side and a second side. The first side and the second side define a cavity therebetween. The second side includes a concave surface defining a recess. The breast pump also includes a breast cup for engaging at least a portion of a breast including a nipple and an area surrounding the nipple. The breast cup is attached to the second side of the housing and positioned at least partly within the recess defined by the concave surface. The breast pump further includes a vacuum pump assembly, a container, a heater mounted to the housing, and a power source. The heater extends along the concave surface of the second side of the housing in thermal connection with the breast cup. The heater is configured to provide heat to the breast cup when the power source provides electrical current to the heater.

18 Claims, 19 Drawing Sheets

(52) U.S. Cl.
CPC ....... *A61M 1/0697* (2021.05); *A61M 2205/36* (2013.01); *A61M 2205/82* (2013.01); *A61M 2207/10* (2013.01)

(58) Field of Classification Search
CPC .... A61M 2207/10; A61M 1/06; A61M 1/062; A61M 1/069; A61M 1/0697; A61M 2205/3368; A61M 2205/3653
See application file for complete search history.

(56) References Cited

U.S. PATENT DOCUMENTS

| | | | |
|---|---|---|---|
| 2004/0087898 A1* | 5/2004 | Weniger | A61M 1/064 604/74 |
| 2006/0247559 A1 | 11/2006 | Fei | |
| 2008/0262419 A1* | 10/2008 | Rollin | A61M 1/066 604/74 |
| 2009/0071952 A1* | 3/2009 | Kuwabara | H05B 1/0233 219/494 |
| 2015/0157775 A1* | 6/2015 | Hu | A61M 1/062 604/74 |
| 2016/0206794 A1* | 7/2016 | Makower | A61M 1/06 |
| 2017/0072118 A1* | 3/2017 | Makower | A61M 1/067 |
| 2020/0155738 A1 | 5/2020 | Makower et al. | |

\* cited by examiner

BREAST PUMP WITH VIBRATION UNIT AND HEATER

CROSS REFERENCE TO RELATED APPLICATION

This application is a U.S. National Phase Application of PCT/US2022/079462, filed on Nov. 8, 2022, which claims the benefit of priority to U.S. Provisional Patent Application No. 63/286,281, filed Dec. 6, 2021. The content of these applications is hereby expressly incorporated by reference in their entirety.

BACKGROUND

The field of this disclosure relates generally to breast pumps and more particularly to a breast pump that includes a vibration unit for vibrating a breast cup assembly and a heater for providing heat to the breast cup assembly during operation.

Electric breast pumps typically include at least one breast cup configured for sealing placement over a nursing woman's breast and a base unit that is connected to the breast cups via tubes. The base unit includes a vacuum pump which is connected to a power source. The vacuum pump within the base is operatively connected to the breast cup via the tubes for applying a vacuum to the nursing woman's breast within the breast cup for extracting milk from the breast. A bottle or other suitable receptacle is in fluid connection with the breast cup to collect the extracted milk. However, a nursing woman may not be able to perform other tasks while using such breast pumps because the breast cups must be held or supported against the breasts and the nursing woman's mobility is limited by the length of the tubes connecting the breast cups to the base unit.

At least some known breast pumps are designed to be portable and do not need to be connected to a stationary base unit during operation. For example, some breast pumps are designed to be worn within a brassiere or other support garment to provide hands-free pumping. These portable breast pumps may be inserted within the brassiere and activated during pumping sessions. However, at least some portable breast pumps may be uncomfortable or awkward to wear within a brassiere or other support garments.

Additionally, some nursing women that use a breast pump may not produce enough milk to satisfy a baby's needs. For example, milk ducts within the breast may become clogged before, during, or after operation of the breast pump, limiting the amount of milk that is extracted by the breast pump. Alternatively, the position and operation of the breast pump may decrease or limit milk production.

Therefore, there is a need for a breast pump that is comfortable and convenient for a woman to wear and that increases milk production.

SUMMARY

In one aspect, a breast pump includes a housing including a first side and a second side opposite the first side. The first side and the second side define a cavity therebetween. The second side includes a concave surface defining a recess. The breast pump also includes a breast cup for engaging at least a portion of a breast surrounding a nipple. The breast cup is attached to the second side of the housing and positioned at least partly within the recess defined by the concave surface. The breast pump further includes a vacuum pump assembly for applying a vacuum to the breast cup and at least the nipple of the breast, a container fluidly connected to the breast cup for receiving milk expressed from the nipple of the breast, a heater mounted to the housing, and a power source mounted within the cavity of the housing and connected to the heater. The heater extends along the concave surface of the second side of the housing in thermal connection with the breast cup. The heater is configured to provide heat to the breast cup when the power source provides electrical current to the heater.

In another aspect, a breast pump includes a housing including a first side and a second side opposite the first side. The first side and the second side define a cavity therebetween. The breast pump also includes a breast cup attached to the housing and shaped to engage at least a portion of a breast surrounding a nipple. The breast pump further includes a vacuum pump assembly for applying a vacuum to the breast cup and at least the nipple of the breast, a container fluidly connected to the breast cup for receiving milk expressed from the nipple of the breast, a vibration unit mounted within the cavity of the housing, a heater mounted to the second side of the housing in thermal connection with the breast cup, and a power source mounted within the cavity of the housing and connected to the vibration unit and the heater. The vibration unit is configured to cause vibration of the breast cup when the power source provides electrical current to the vibration unit. The heater is configured to provide heat to the breast cup when the power source provides electrical current to the heater.

In yet another aspect, a method of assembling a breast pump includes providing a housing including a first side and a second side opposite the first side. The first side and the second side define a cavity therebetween. The second side includes a concave surface defining a recess. The method also includes attaching a breast cup to the second side of the housing such that the breast cup is positioned at least partly within the recess defined by the concave surface, connecting a vacuum pump assembly to the breast cup for applying a vacuum to the breast cup and at least the nipple of the breast, fluidly connecting a container to the breast cup for receiving milk expressed from the nipple of the breast, and attaching a heater to the housing. The heater extends along the concave surface of the second side of the housing in thermal connection with the breast cup. The method also includes connecting a power source to the heater. The power source is mounted within the cavity of the housing. The heater is configured to provide heat to the breast cup when the power source provides electrical current to the heater.

DETAILED DESCRIPTION OF THE DRAWINGS

Figure 1:
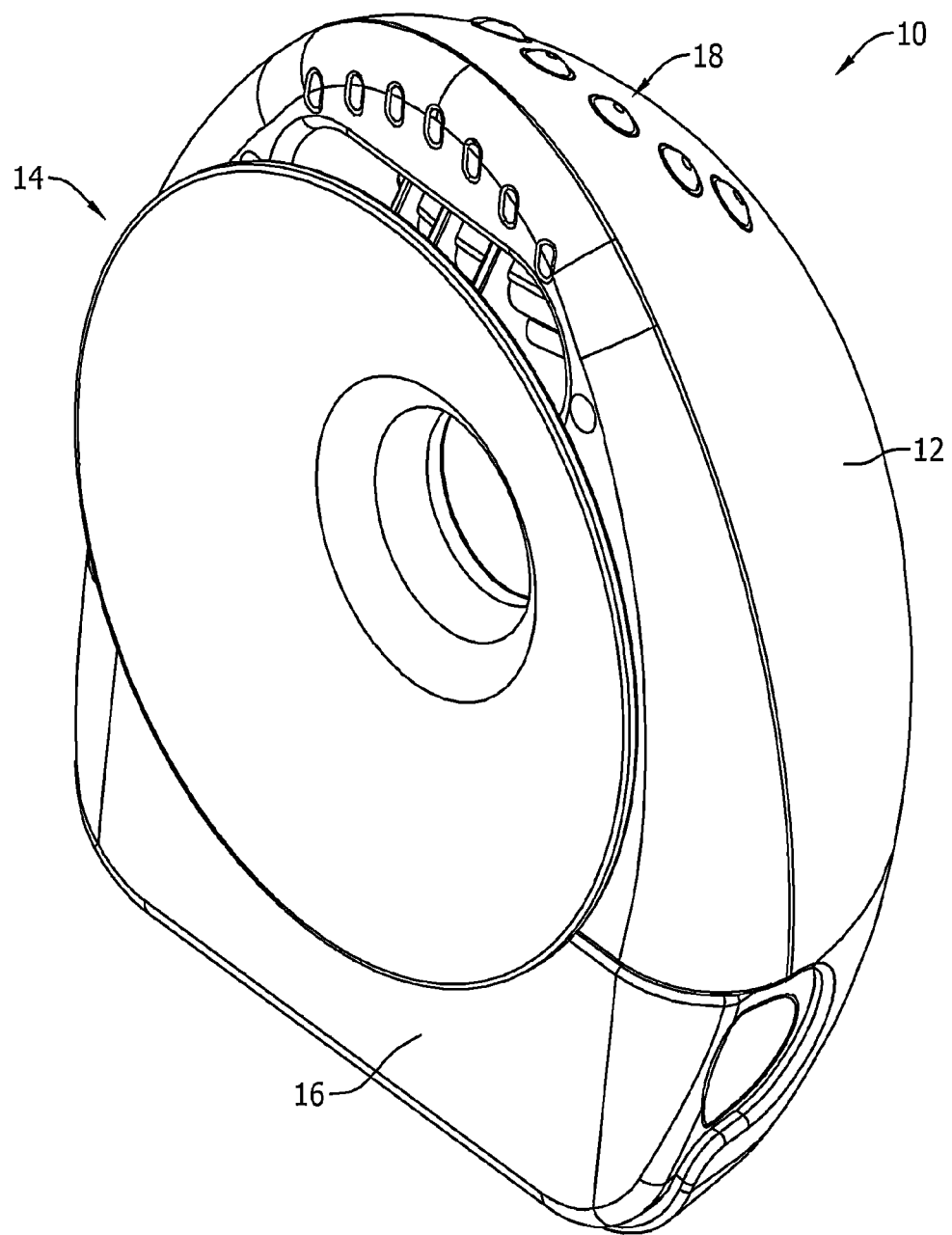
FIG. 1 is a rear perspective of one suitable embodiment of a wearable electric breast pump having a breast cup assembly, a vibration unit for vibrating the breast cup assembly, and a heater for providing heat to the breast cup assembly.
Figure 19:
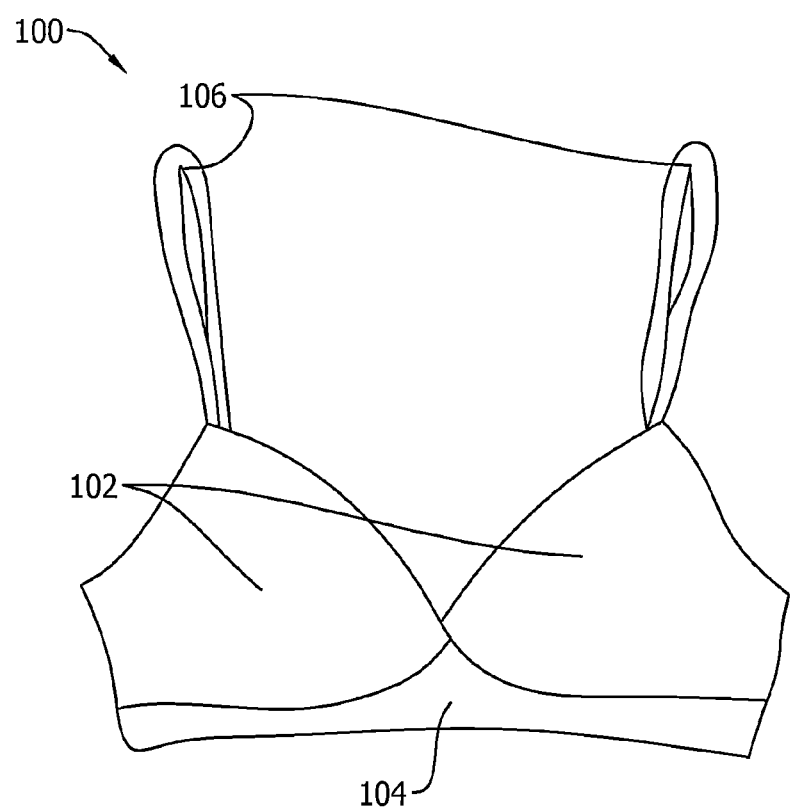
FIG. 19 is a front view of one suitable embodiment of a brassiere, the breast pump being configured to be worn within the brassiere for hands free pumping.

With reference now to the accompanying drawings, and specifically to FIG. 1, a wearable electric breast pump according to one suitable embodiment of the present disclosure is illustrated and is indicated generally at 10. Although aspects of this disclosure are described with reference to a wearable electric breast pump, it should be understood that the disclosure is not so limited, and aspects of this disclosure may be used with any suitable type of breast pump including both electric and manual breast pumps and/or with an attachment or collection kit for a breast pump. For example, in some embodiments, components of the breast pump 10 such as the container, the vibration unit, and the heater are included in a collection attachment that is arranged to attach to a breast pump. In some embodiments, the breast pump 10 is provided in a pair of breast pumps. In addition, the breast pump 10 is arranged to be worn within a brassiere or other support garment and provide hands-free pumping. For example, FIG. 19 illustrates one suitable embodiment of a brassiere 100 for use with the breast pump 10. The brassiere 100 includes cups 102 that receive a wearer's breasts, a support band 104, and straps 106. The breast pump 10 is arranged to be worn within the cups 102 of the brassiere 100 and engaged with the breasts within the cups 102 to provide hands-free pumping.

As seen in FIG. 1, the breast pump 10 includes a suitable housing, indicated generally at 12, for housing various working components such as a pump or pumps, a controller, and other components as will be described later herein. The breast pump 10 also comprises a breast cup assembly 14 for receiving a nursing woman's breast, and a container 16 for receiving milk expressed from the nursing woman's breast. The breast cup assembly 14 is in fluid communication with the container 16, such as via a fluid path as described further herein, so that milk expressed from the breast cup assembly 14 is collected in the container 16.

Figure 7:
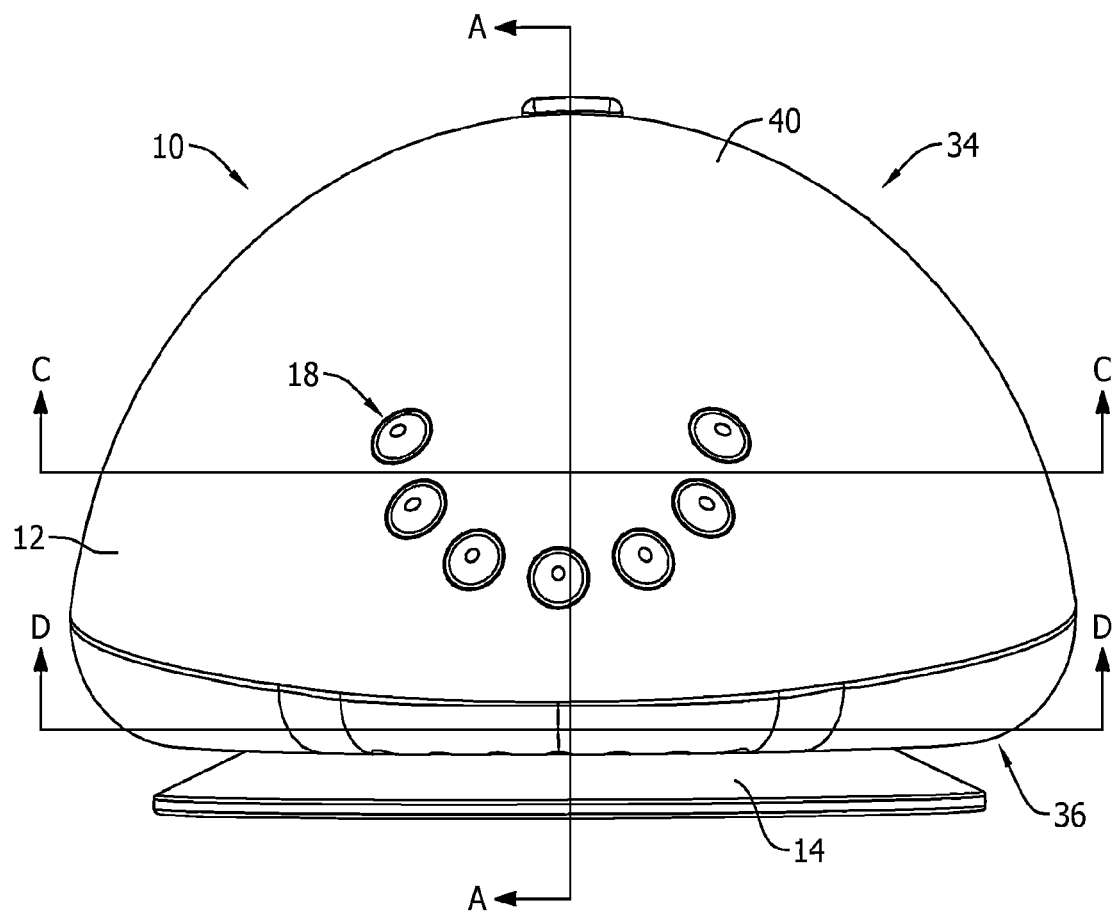
FIG. 7 is a top view of the breast pump.
Figure 8:
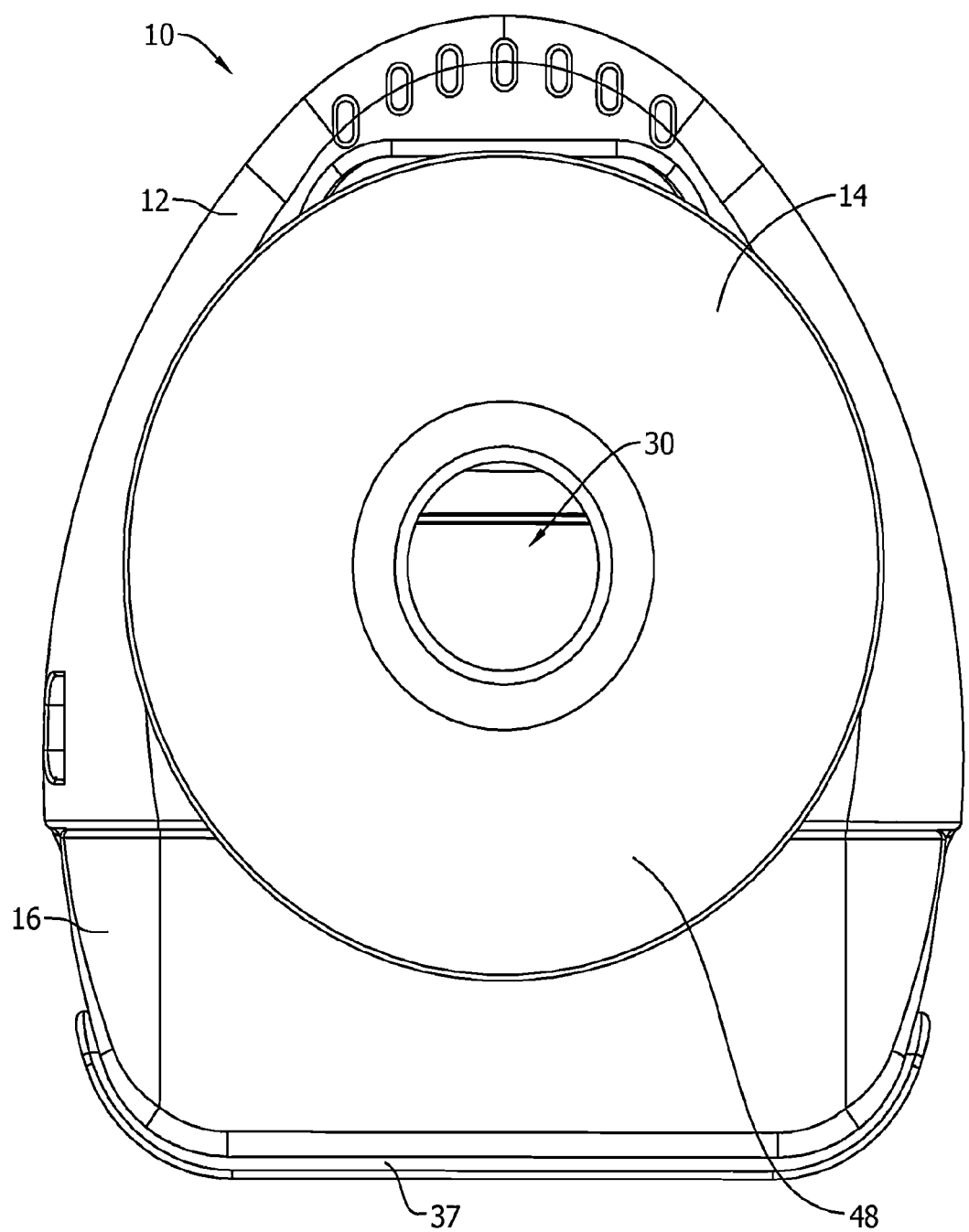
FIG. 8 is a rear view of the breast pump.
Figure 9:
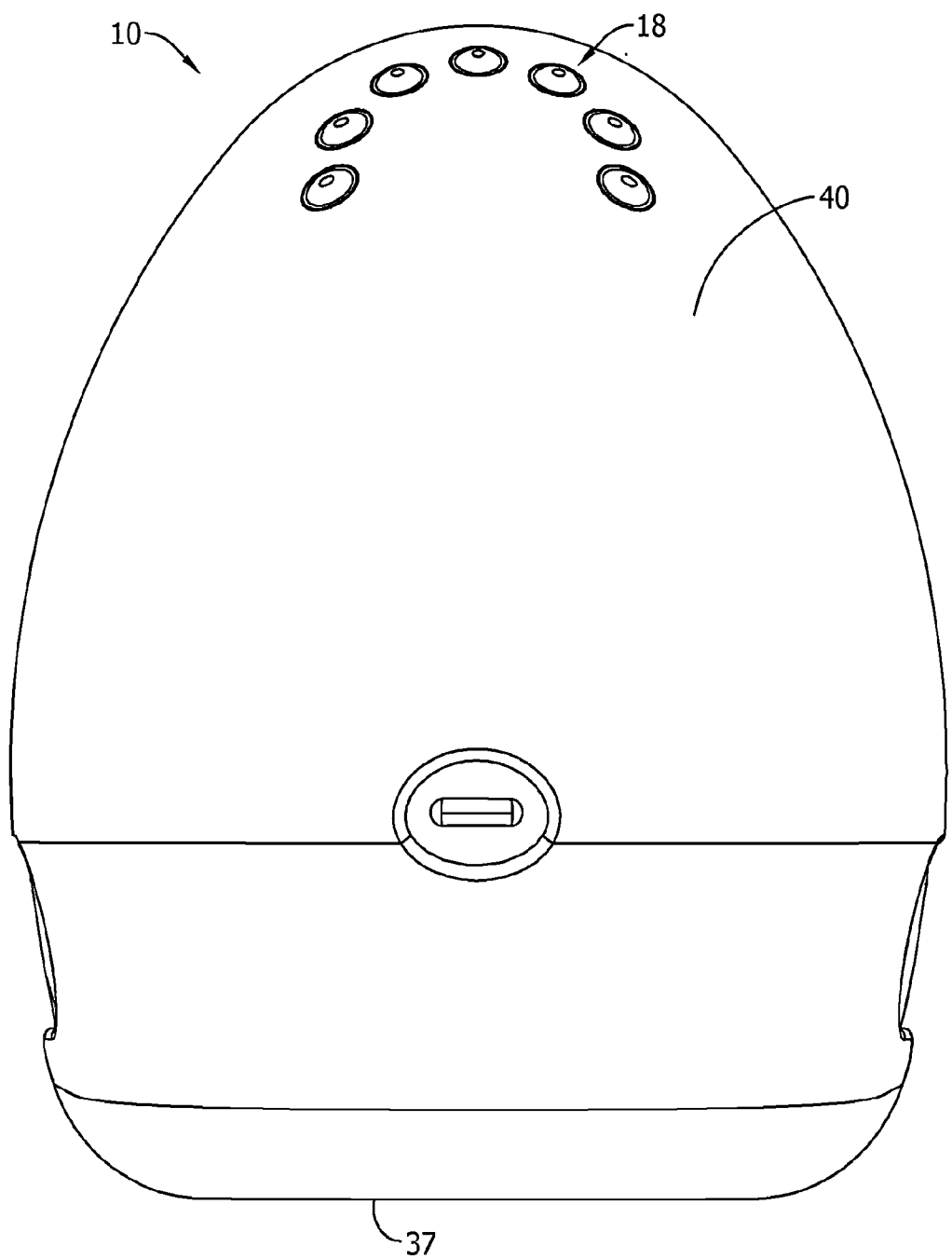
FIG. 9 is a front view of the breast pump.
Figure 10:
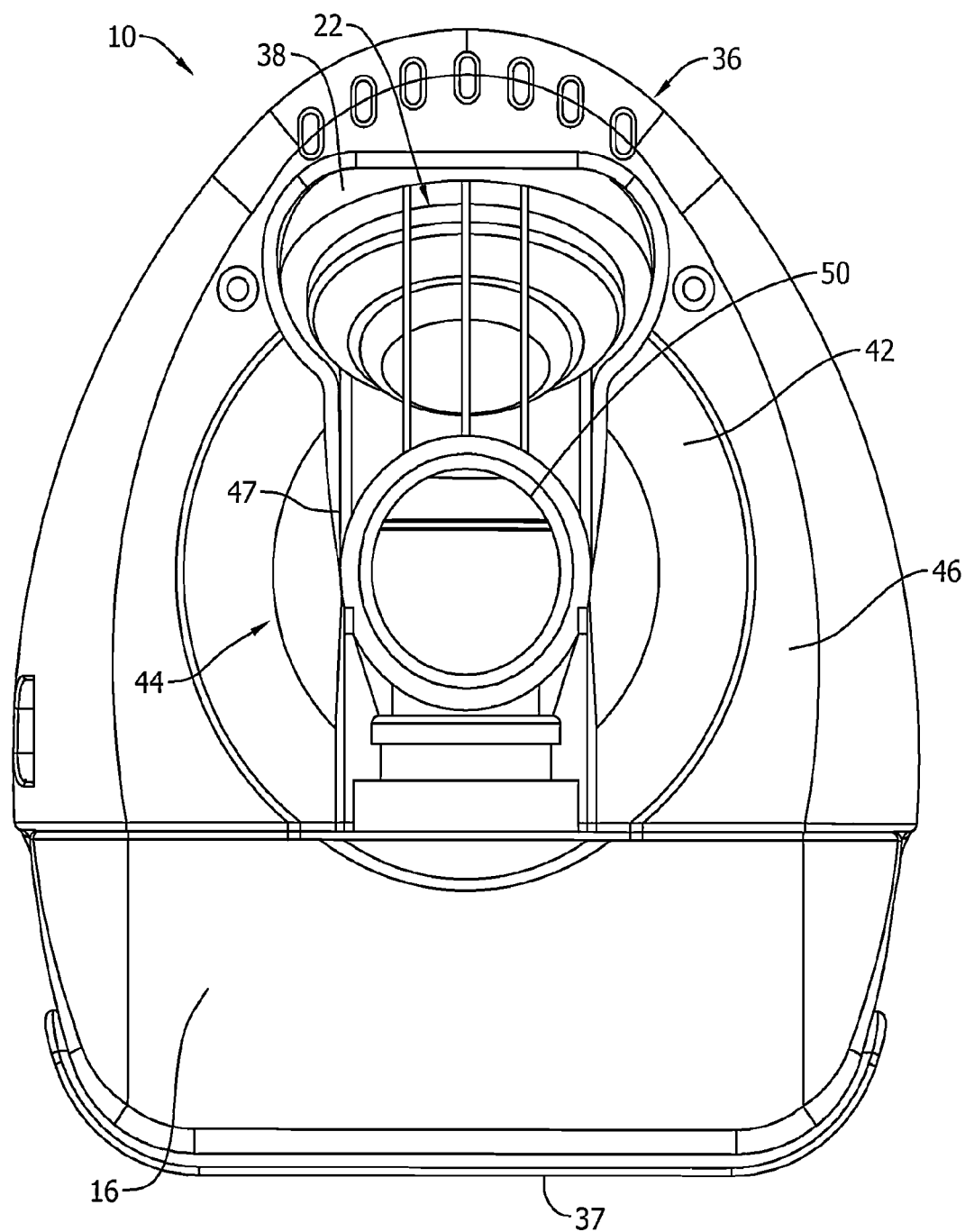
FIG. 10 is a rear view of the breast pump, with the breast cup assembly removed to illustrate a curved surface of a housing of the breast pump.

As best seen in FIGS. 7 and 9, a user interface 18 is positioned on the housing 12 of the breast pump 10. In one suitable embodiment, the user interface 18 includes a display for displaying information to the user and/or one or more buttons for receiving input from the user. Some embodiments may communicate with a remote device (such as a mobile phone, tablet, desktop computer, laptop computer, or the like) and utilize the remote device as a user interface instead of or in addition to the user interface 18 positioned on the housing 12.

Figure 2:
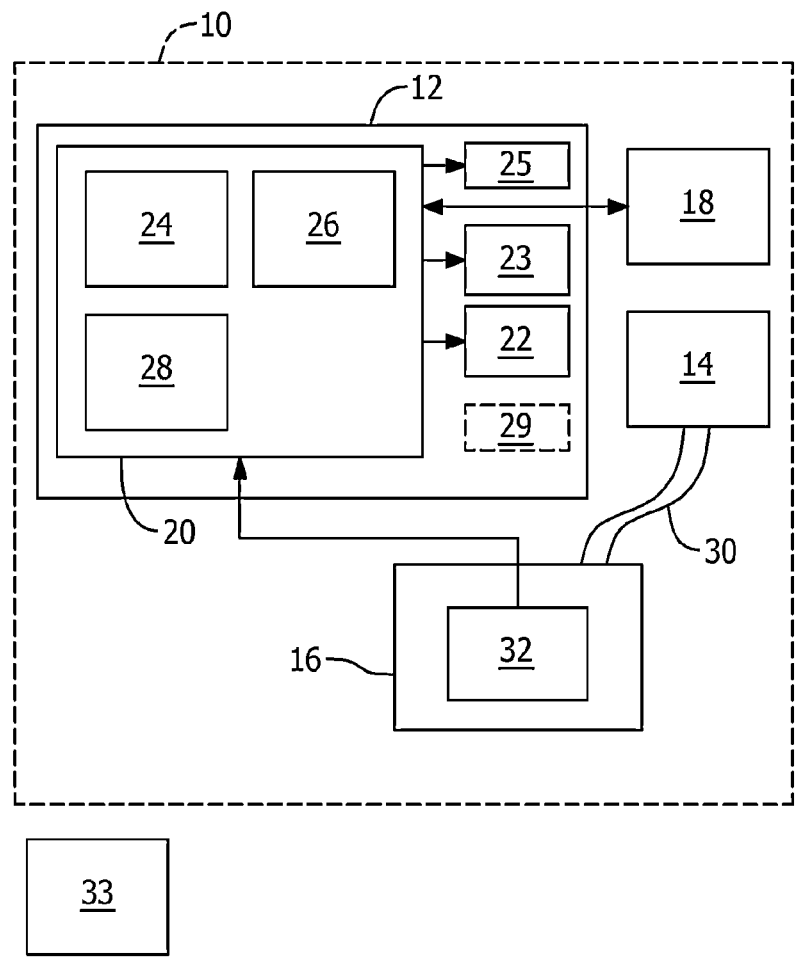
FIG. 2 is a simplified schematic diagram of the breast pump.

FIG. 2 is a simplified schematic diagram of the breast pump 10 of FIG. 1. The housing 12 of the breast pump 10 encloses a controller 20, a vacuum pump assembly 22, a vibration unit 23, and a heater 25. The controller 20 includes a processor 24, a memory 26, and a communications interface 28. The vacuum pump assembly 22 includes at least one vacuum pump, and may include other components to aid in controlling the vacuum produced by the vacuum pump. Moreover, the vacuum pump assembly 22 may include one or more positive pressure pumps to apply positive pressure to portions of the breast cup assembly 14 to mimic more closely a baby breastfeeding. The breast pump 10 optionally includes a tilt sensor 29 to detect an orientation of the breast pump (e.g., level or some angle off of level in the X-Y plane of the breast pump).

In general, instructions stored in the memory 26, when executed by the processor 24, configure the controller 20 to control operation of the breast pump 10. The controller 20 is communicatively coupled to the vacuum pump assembly 22 and controls operation of the vacuum pump assembly 22 according to the instructions stored in the memory 26 and according to user input through the user interface 18. The user interface 18 is attached to the housing 12 and communicatively coupled to the controller 20. In some embodiments, the breast pump 10 includes more than one vacuum pump assembly 22 controlled by the controller 20. The breast cup assembly 14 is attached to the housing 12 of the breast pump and in communication with the vacuum pump assembly 22 to allow the vacuum pump assembly 22 to apply a vacuum to the breast cup assembly 14. Also, the breast cup assembly 14 is in fluid communication with the container 16 through a fluid path 30. In some embodiments, a sensor assembly 32 is positioned in the container 16 and communicatively coupled to the controller 20.

As used herein, a "processor" may be one or more central processing units, microprocessors, microcontrollers, reduced instruction set circuits (RISC), application specific integrated circuits (ASIC), logic circuits, and any other circuit or processor capable of executing the functions described herein. A "memory" may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above are examples only and are thus not intended to limit in any way the definition and/or meaning of the terms "processor" or memory. In some embodiments, the processor 24 and the memory 26 are separate components, while in other embodiments, the processor 24 and the memory 26 are part of a single component, such as in a microcontroller. In the example, the communications interface 28 is a wireless communications module. In other embodiments, the communications interface 28 may be any suitable wired or wireless communications module.

In the example, the communications interface 28 comprises a Bluetooth® adapter. In other embodiments, the communications interface 28 may include one or more of a radio frequency (RF) transceiver, a Bluetooth® adapter, a Wi-Fi transceiver, a ZigBee® transceiver, an infrared (IR) transceiver, and/or any other device and communication protocol for wireless communication. (Bluetooth is a registered trademark of Bluetooth Special Interest Group of Kirkland, Washington: ZigBee is a registered trademark of the ZigBee Alliance of San Ramon, California.) In embodiments using wired communication interfaces, any suitable wired communication protocol for direct communication may be used including, without limitation, USB, RS232, I2C, SPI, analog, and proprietary I/O protocols. In some embodiments, the wired communication interface includes a wired network adapter allowing the controller to be coupled to a network, such as the Internet, a local area network (LAN), a wide area network (WAN), a mesh network, and/or any other network to communicate with remote devices and systems via the network.

The communications interface 28 allows the controller to communicate with a user's remote device 33. In the examples, the remote device 33 is a mobile phone or a tablet computer. In some embodiments, the remote device 33 is a laptop computer, a desktop computer, a personal digital assistant (PDA), or any other device operable to receive data, display data, and/or receive user input.

As seen in FIGS. 3-10, the housing 12 includes a first side 34, a second side 36 opposite the first side 34, and a bottom 37 extending between the first side 34 and the second side 36. The first side 34, the second side 36, and the bottom 37 collectively define a cavity 38 (seen in FIG. 10) therebetween. The first side 34 and the second side 36 are at least partly curved. For example, in the illustrated embodiment, the first side 34 includes a convex surface 40 that extends throughout the first side 34, and the second side 36 includes a concave surface 42 that is surrounded by a generally planar surface 46. The concave surface 42 of the second side 36 defines a recess 44 (best seen in FIG. 10). In addition, the second side 36 defines a slot 47 that extends through the recess 44 and is sized to receive the connector 50 attached to the breast cup 48. As a result, the housing 12 facilitates the breast pump 10 being compact and sized to fit within a brassiere. For example, in use, the breast pump 10 is sized to fit within a brassiere (e.g., the brassiere 100 shown in FIG. 19) such that the first side 34 contacts the brassiere and the second side 36 is positioned proximate the nursing woman's breast. In particular, the housing 12 is cup-shaped to correspond to a cup (e.g., cup 102 shown in FIG. 19) of the brassiere. In addition, the housing 12 is sized and shaped to enclose components such as the vacuum pump assembly 22, the vibration unit 23, and the heater 25.

Figure 11:
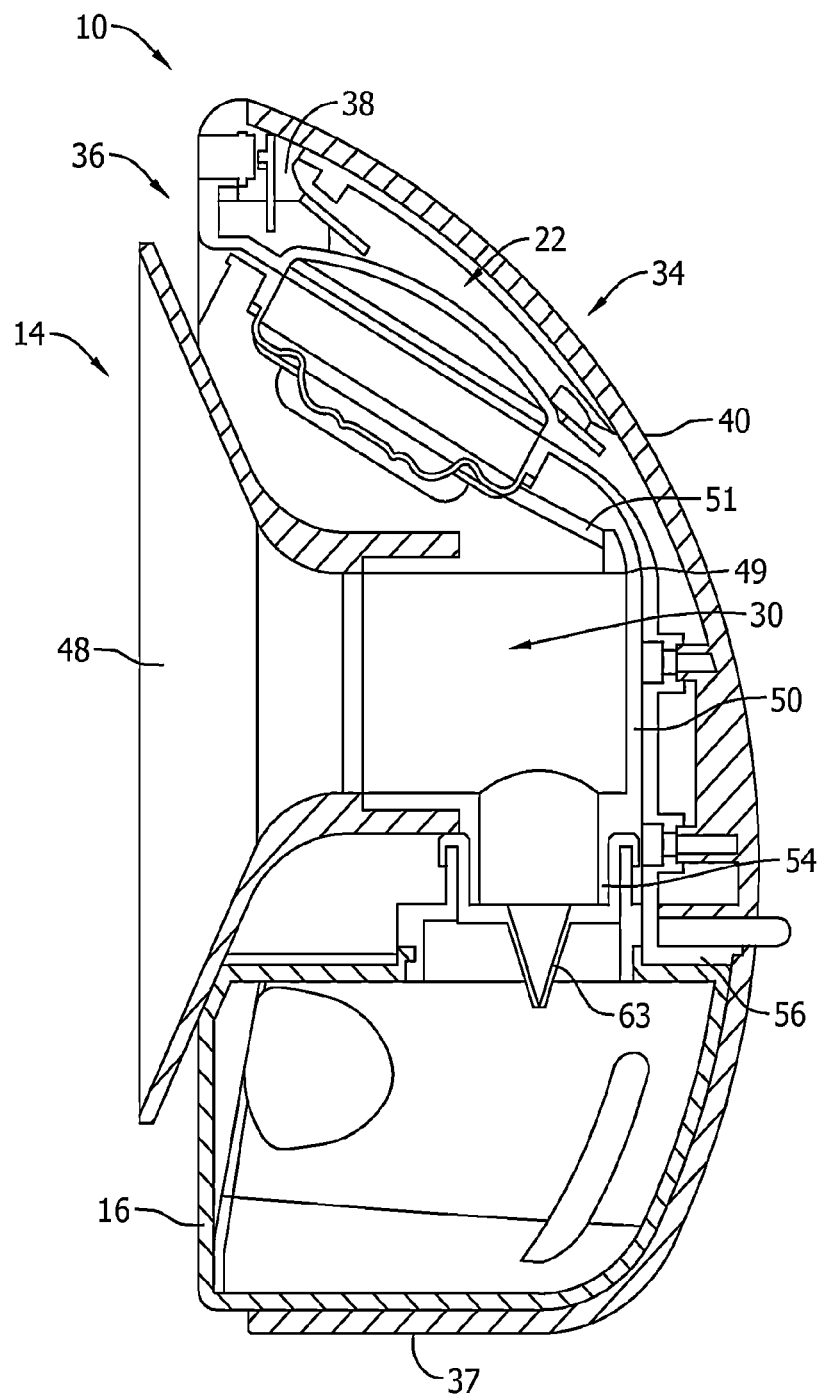
FIG. 11 is a cross-section of the breast pump, taken along A-A in FIG. 7.
Figure 12:
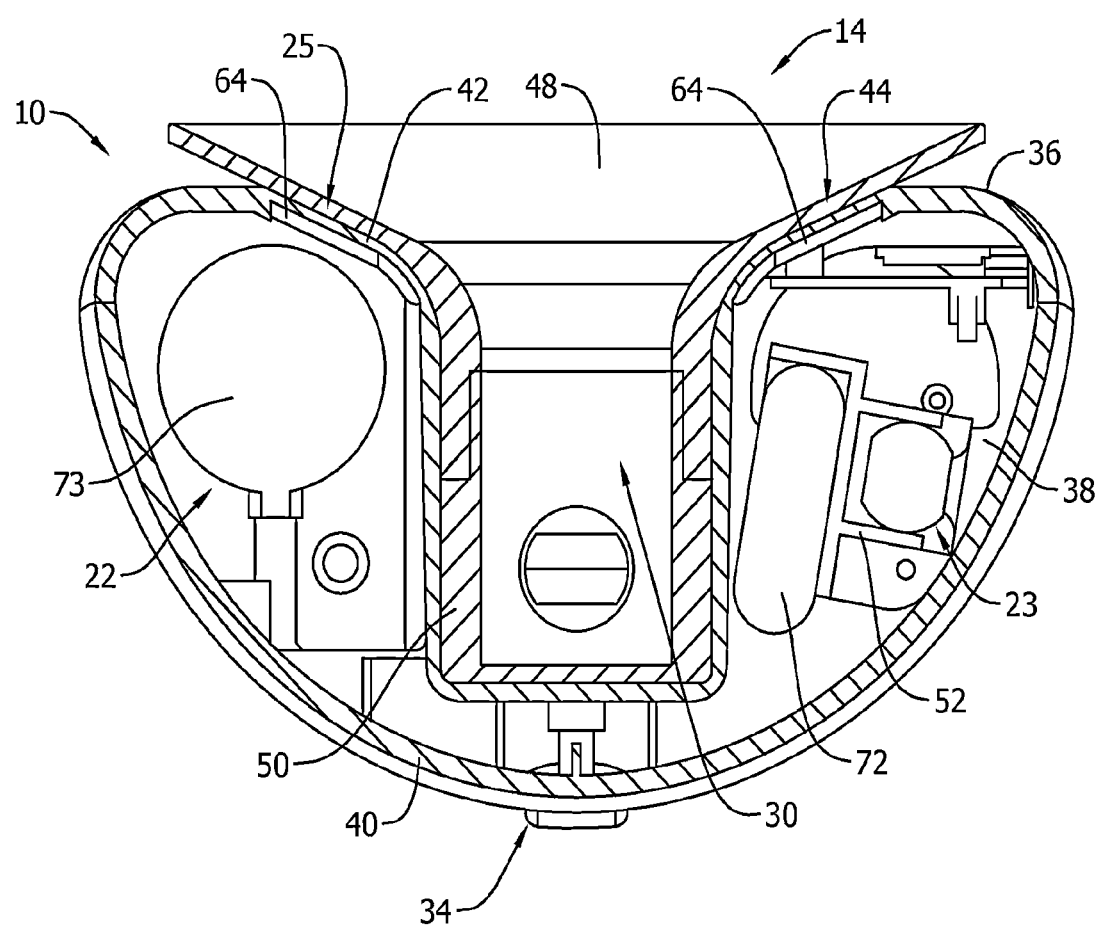
FIG. 12 is a cross-section of the breast pump, taken along B-B in FIG. 4.

Referring to FIGS. 11 and 12, the breast cup assembly 14 is attached to the housing 12 and enclosed partly within the housing 12. The breast cup assembly 14 includes a breast cup 48 and a connector 50 connected to the breast cup 48. The breast cup 48 is sized and shaped to engage at least a portion of a breast including a nipple and an area surrounding the nipple. In the illustrated embodiment, the breast cup 48 is generally a hollow frustum. In one suitable embodiment, the breast cup 48 is constructed of silicone. In other embodiments, the breast cup 48 may have other materials or shapes without departing from aspects of the disclosure.

The breast cup assembly 14 is attached to the housing 12 such that the housing 12 at least partly surrounds the breast cup 48. Specifically, the breast cup 48 is attached to the second side 36 of the housing 12 and positioned within the recess 44 defined by the concave surface 42 of the second side 36 of the housing 12. The concave surface 42 extends partly around the breast cup 48. The breast pump 10 is arranged to be worn such that the second side 36 of the housing 12 is positioned proximate a breast and the breast cup 48 engages the breast.

As illustrated in FIG. 11, the connector 50 is attached to an end of the breast cup 48 and extends through the slot 47 of the housing 12 toward the first side 34 of the housing 12. The connector 50 at least partly defines the fluid path 30 that connects the breast cup 48 to the container 16. The vacuum pump assembly 22 is attached to the top of the connector 50 in fluid communication with the breast cup 48. For example, an opening 49 is defined in the top of the connector 50 and is connected by a passage 51 to the vacuum pump assembly 22. The vacuum pump assembly 22 is operable to generate a vacuum in the cavity of the connector 50 and the breast cup 48 to provide vacuum to the breast and, thereby, facilitate the expression of milk from the breast.

With reference still to FIG. 11, the container 16 is connected to an outlet 54 on a bottom of the connector 50 and arranged to receive milk that is expressed from the breast. A valve 63 (e.g., a duck-bill valve) is positioned on the outlet 54 of the connector 50 to regulate milk flow into the container 16 and prevent overflow or spillage of the milk within the container 16. The illustrated container 16 includes one or more curved walls and is sized to fit within a space defined between the bottom 37 and a wall 56 of the housing 12. The container 16 is selectively removable from the housing 12 by removing the connector 50, the breast cup 48, and the valve 63. In other suitable embodiments, the breast pump 10 may include a different container 16 without departing from aspects of the disclosure. For example, in some embodiments, the container 16 is defined by a part of the housing 12. In further embodiments, a flexible receptacle such as a bag is attached to the outlet 54 to receive the milk.

As best seen in FIG. 12, a power source 72 is positioned within the cavity 38 of the housing 12 and connected to one or more components of the breast pump 10. For example, the power source 72 is connected to the vibration unit 23, the heater 25, and a motor 73 of the pump assembly 22. The breast pump 10 is more compact than other breast pumps because the power source 72 provides power to multiple components. In the illustrated embodiment, the power source 72 comprises a battery that is mounted within the cavity 38 and adjacent to the vibration unit 23. The battery may be rechargeable. The power source 72 is configured to provide electrical current to the components of the breast pump 10 during operation. For example, the power source 72 provides electrical current to the vibration unit to cause the vibration unit 23 to vibrate the housing 12 and thereby the breast cup assembly 14. Also, the power source 72 provides electrical current to the heater 25 to cause the heater 25 to deliver heat to the breast cup assembly 14 to warm the breast.

Figure 13:
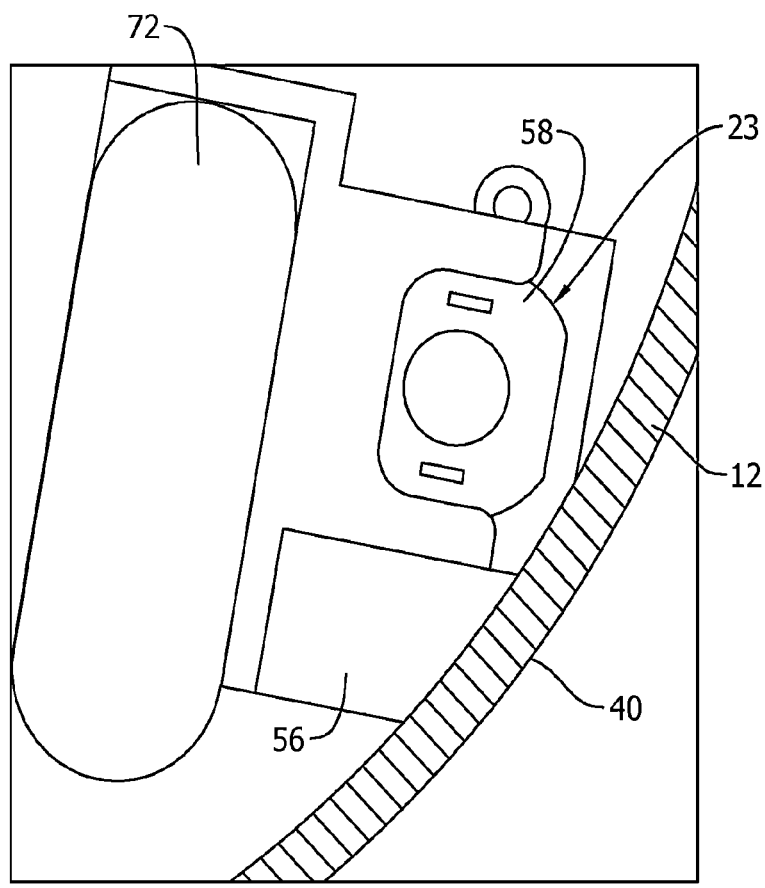
FIG. 13 is an enlarged cross-section of a portion of the breast pump, illustrating the vibration unit and a power source of the breast pump.
Figure 14:
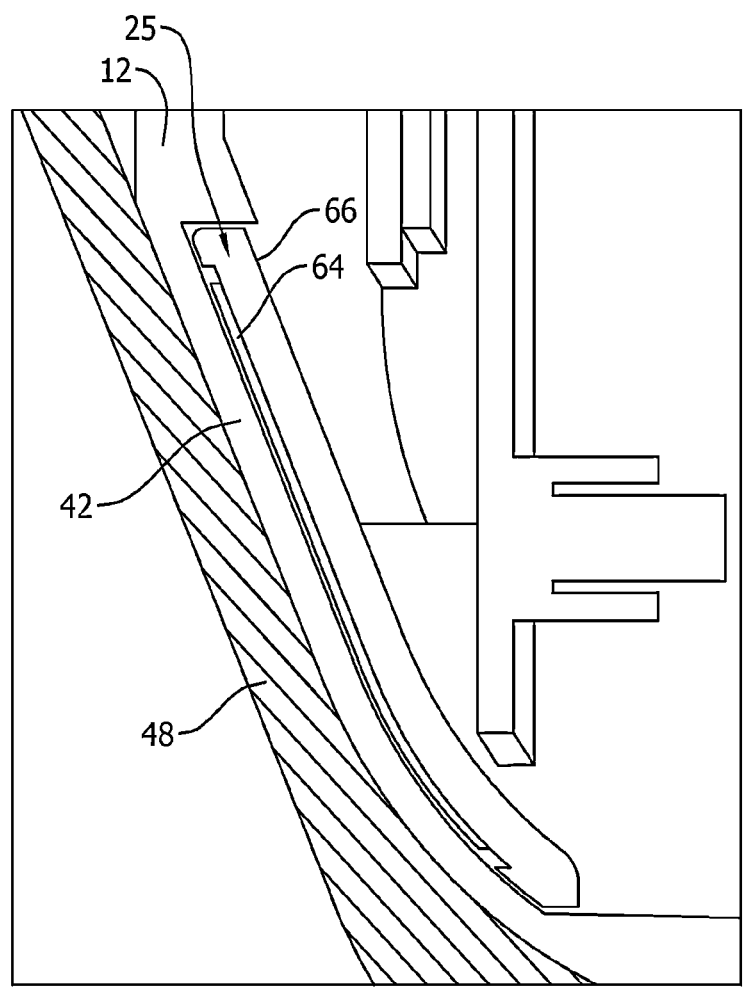
FIG. 14 is an enlarged cross-section of a portion of the breast pump, illustrating a portion of the heater.
Figure 17:
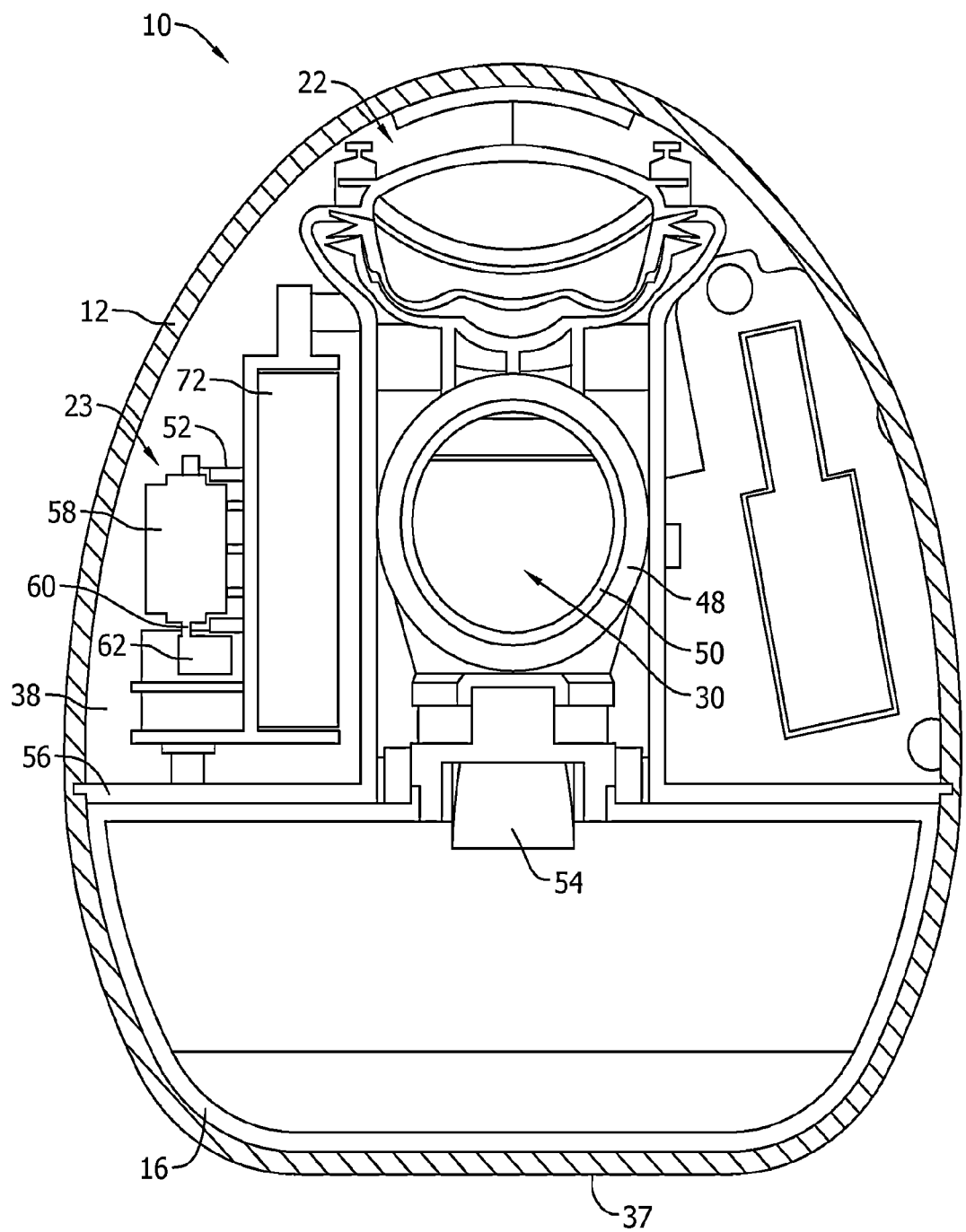
FIG. 17 is a cross-section of the breast pump, taken along line C-C in FIG. 7 and illustrating a pump assembly and a vibration motor of the vibration unit.
Figure 18:
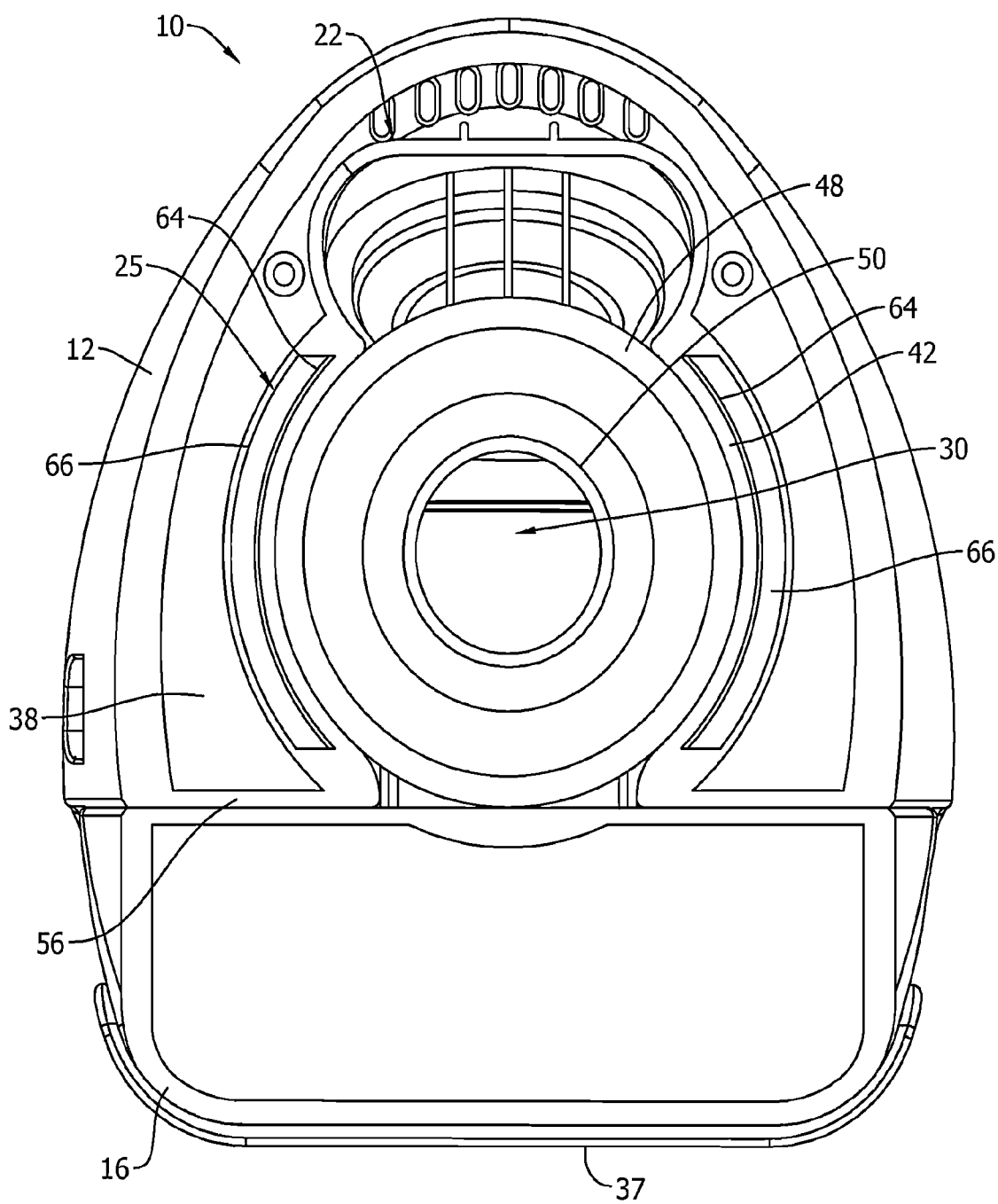
FIG. 18 is a cross-section of the breast pump, taken along line D-D in FIG. 7 and illustrating heating elements of the heater.

With reference to FIGS. 12, 13, and 17, the vibration unit 23 includes a motor 58 connected to a rotor 60 and an eccentric weight 62 connected to the rotor 60. The rotor 60 is a rotatable shaft that is rotated by the motor 58. The rotor 60 is connected to the eccentric weight 62 at a location that is not at the center of mass of the eccentric weight 62. Accordingly, the center of mass of the eccentric weight 62 shifts within the cavity 38 of the housing 12 as the rotor 60 and the eccentric weight 62 are rotated by the motor 58. The shifting of the center of mass of the eccentric weight 62 causes vibrations within the breast pump 10. In other embodiments, the breast pump 10 includes other vibration units without departing from some aspects of the disclosure. For example, in some embodiments, the vibration unit 23 is incorporated into the motor 73 of the vacuum pump assembly 22.

The vibration unit 23 is mounted within the cavity 38 of the housing 12 to transfer vibrations to the housing 12.

Specifically, the vibration unit 23 is mounted to a frame 52 that is secured to at least one wall 56 extending between the first side 34 and the second side 36 of the housing 12. The frame 52 is configured to secure the vibration unit 23 in position and transfer vibrations to the housing 12. For example, the frame 52 is rigid and is rigidly secured to the wall 56 to transfer vibrations therethrough. During operation, the motor 58 of the vibration unit 23 induces rotation of the rotor 60 and the eccentric weight 62 which vibrates the rigid frame 52, the wall 56, and, thereby, the housing 12. The housing 12 transfers the vibrations to the breast cup 48 and to a breast engaged with the breast cup. The vibrations can facilitate an increase in the milk production and facilitate unclogging of milk ducts within the breast. For example, the vibration unit 23 vibrates the breast which can dislodge obstructions within the milk ducts and provide improved milk flow through the milk ducts within the breast. In addition, the vibrations from the vibration unit 23 facilitate the breast being more effectively emptied during pumping.

Referring now to FIGS. 14-16 and 18, the heater 25 includes a pair of heating elements 64 that are spaced apart. The heating elements 64 are mounted to the second side 36 of the housing 12 proximate to the breast cup 48 and spaced apart on opposite sides of the connector 50, and, therefore, opposite sides of a nipple when the breast cup 48 is placed into engagement with a breast. The heating elements 64 of the heater 25 are mounted in thermal connection with the breast cup assembly 14. Specifically, the heating elements 64 are mounted to the concave surface 42 of the second side 36 of the housing 12 proximate the breast cup 48. The second side 36 and/or the heater 25 is in contact with the breast cup 48 to transfer heat from the heating elements 64 to the breast cup 48. In some embodiments, the second side 36 of the housing 12 includes an insulation material, i.e., a material with a lower heat conductance than the heating elements 64. The insulation material can facilitate a reduction of the amount of heat that is transferred to the breast cup 48 and the prevention of overheating of the breast cup. Insulation sheets 66 are positioned on surfaces of the heating elements 64 opposite the breast cup 48 to reduce the transfer of heat to components within the cavity 38 of the housing 12. The heating elements 64 are arranged to facilitate the targeted delivery of heat to the breast while facilitating a reduction of wasted heat that is transferred to other components. In addition, the heating elements 64 require less power to operate than other heaters.

Figure 15:
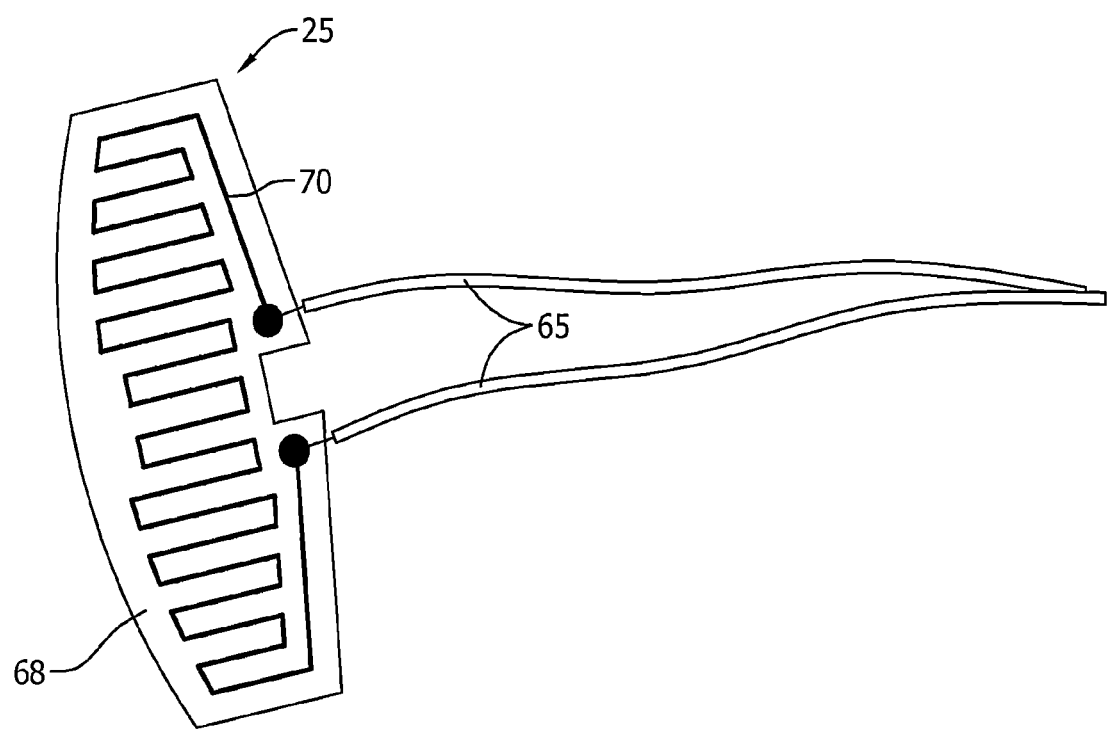
FIG. 15 is a perspective view of a portion of the heater of the breast pump.
Figure 16:
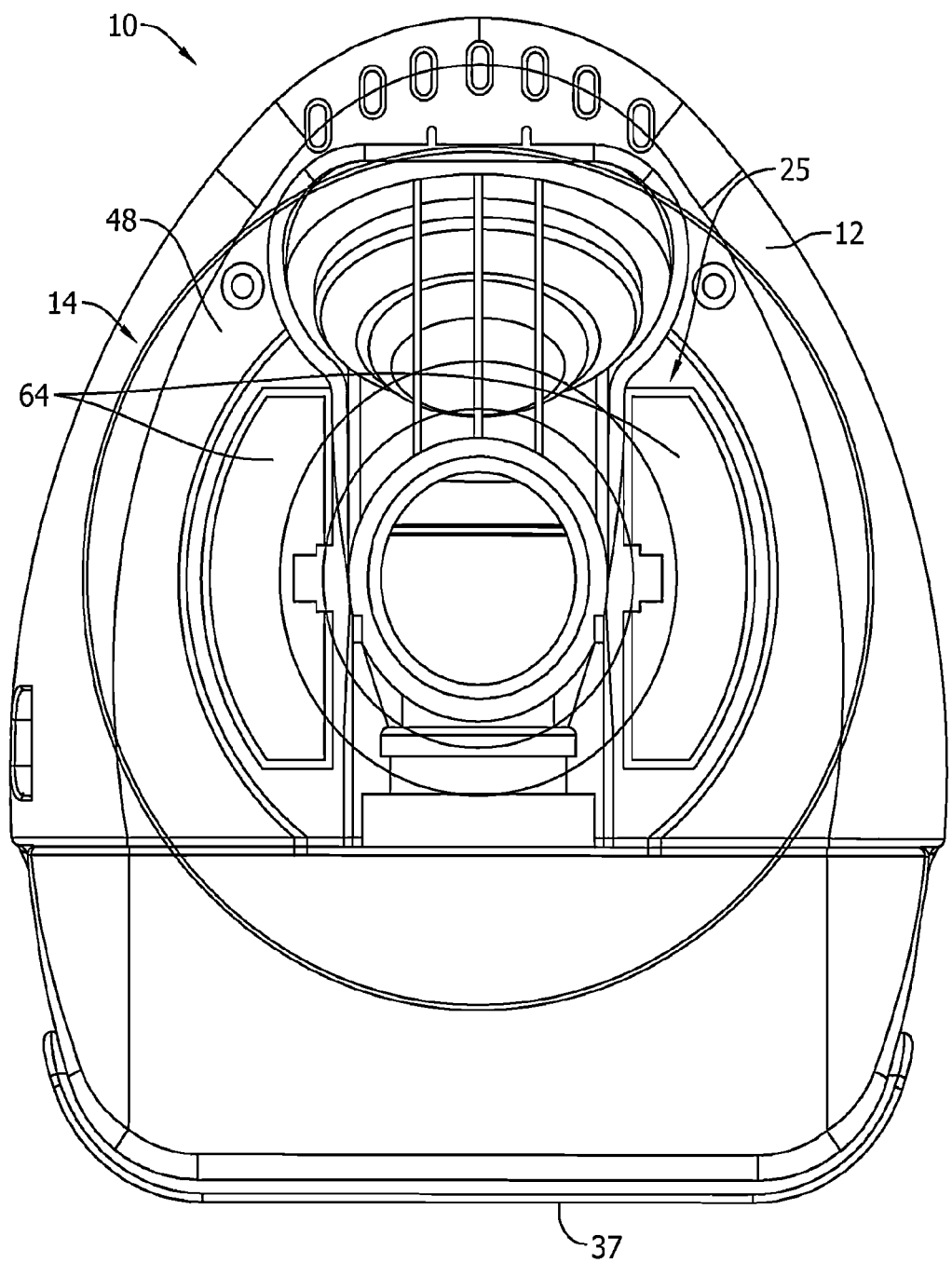
FIG. 16 is a rear view of the breast pump, with the breast cup assembly and the housing made transparent to illustrate heating elements of the heater arranged along the breast cup assembly.

In the example, the heating elements 64 are constructed and shaped to extend at least partly around the breast cup 48. For example, the heating elements 64 are curved to correspond to the radius of the breast cup 48 such that an edge of each of the heating elements 64 is parallel to an edge of the breast cup 48. In the illustrated embodiment, the heating elements 64 comprise a flexible film 68 and resistance wires 70 attached to the flexible film 68 (FIG. 15). The flexible film 68 bends to follow the concave surface 42 of the second side 36 of the housing 12. In one suitable embodiment, the flexible film 68 is a polyimide film. The flexible film 68 may have a width in a range of 10 millimeters (mm) to 50 mm or 15 mm to 20 mm. The flexible film 68 may have a length in a range of 10 mm to 100 mm or 55 mm to 65 mm. In the example, the flexible film 68 has a width of 17 mm and a length of 57 mm. The resistance wires 70 have a resistance of at least 1 ohm for a voltage of at least 1 voltage direct current (VDC). In the example, the resistance wires 70 have a resistance of 5 ohms for a voltage of 3.7 VDC. In other embodiments, the heating elements 64 are constructed in different manners without departing from some aspects of the disclosure.

With reference still to FIG. 15, leads 65 extend from each of the heating elements 64 and are arranged to connect to the power source 72 for delivering electrical current to the heating elements 64. For example, the electrical current flows through the leads 65 from the power source 72 to the resistance wires 70 of the heating elements 64. The electrical current flows through the resistance wires 70 and generates heat in the heating elements 64. The heat generated by the heating elements 64 is transferred through the housing 12 and the breast cup 48, which are in thermal connection with the heating elements 64, to a breast engaged with the breast cup 48. Accordingly, the heater 25 is arranged to deliver heat to the breast for a more comfortable and therapeutic experience for users. In addition, the heater 25 can facilitate increased milk production for the nursing woman. The heat treatment can cause the milk to flow better through milk ducts in the breast because the milk is warmed to a temperature that flows better and the breast is more relaxed in the heated state. In addition, the heat treatment can prevent milk ducts from becoming clogged and can relieve the discomfort of existing clogged milk ducts.

Referring again to FIG. 2, in general during operation of the breast pump 10, the controller 20 is configured, by the instructions stored in the memory 26 and executed by the processor 24, to operate the vacuum pump assembly 22 to apply a vacuum to the breast cup assembly 14. The breast pump operates in a number of stages or modes. The controller 20 begins to operate the vacuum pump assembly 22 to cyclically apply and relax vacuum to the breast cup assembly and thereby to at least the nipple of the breast. At this initial stage, the controller 20 operates the vacuum pump assembly 22 at a first operating mode. In the example, the first operating mode is a stimulating mode of a pumping cycle of the breast pump. The stimulating mode is designed to mimic an infant's initial suckling (e.g., non-nutritive suckling), which causes the woman to experience "letdown." "Letdown" occurs when milk within the woman's breast flows toward the nipple.

In the stimulating mode, the vacuum pump assembly 22 is operated to apply a suction (e.g., maximum) vacuum to the woman's breast. For example, a maximum vacuum in the range of about 30 mm Hg to about 200 mm Hg is applied to the breast. In one particularly suitable embodiment, the suction vacuum is applied to the woman's breast continuously throughout the cycle. It is understood, however, that the suction vacuum can be selectively varied through the cycle. The controller 20 continues to operate the vacuum pump assembly 22 in the first operating mode until the woman experiences letdown. The controller 20 may determine the occurrence of letdown using one or more sensors and/or based on predetermined time cycles.

The second operating mode is an expressing mode. The expressing mode of the pumping cycle is suitably designed to simulate the suckling action and frequency of a nursing infant, e.g., the peristaltic movement of the infant's tongue and palate used to express milk. In particular, during each cycle the vacuum pump assembly 22 is operated to apply a suction (e.g., maximum) vacuum to the woman's breast. For example, a vacuum in the range of about 30 mm Hg to about 280 mm Hg is applied. In one example, the suction vacuum is applied to the woman's breast in the range of about 50 to about 80 percent of each cycle, and more suitably about 72 percent of each cycle. As used herein, a cycle of the vacuum pump assembly 22 includes one suction period, during which a suction vacuum is applied, and one release period, during which no suction vacuum is applied.

In some embodiments, the controller 20 determines an amount of milk pumped and/or a rate of flow of the milk. This rate of flow may be used by the controller 20 to tailor the second operating mode to the particular user (such as to attempt to increase the flow if the flow rate is low or to increase the comfort by decreasing the vacuum if the rate is relatively high), to estimate the remaining time needed to fill the container 16, and/or to inform the user about the rate of flow of milk.

When the controller 20 determines that the amount of milk in the container 16 has reached a threshold value and/or when a preset time has elapsed, the controller 20 stops the pumping session by stopping operation of the vacuum pump assembly 22. The threshold value of the milk in the container 16 is a value that is substantially the maximum recommended volume of the container (which may be less than the volume of the container in order to avoid spilling or overfilling).

Before, during, or after operation of the vacuum pump assembly 22, the controller 20 is configured to operate the vibration unit 23 to deliver vibrations to the breast. For example, the controller 20 controls the current that is provided from the power source 72 to the motor 58 to cause the eccentric weight 62 to oscillate at a desired frequency that is therapeutic for the breast. The controller 20 can operate the vibration unit 23 in coordination with the pump stages of the vacuum pump assembly 22 and/or based on a user input. For example, the controller 20 can operate the vibration unit 23 before or during the stimulating mode and/or the operating mode of the vacuum pump assembly 22. Alternatively or additionally, the controller 20 can operate the vibration unit 23 based on a user selection of a vibrating mode that is input by the user via the user interface 18. In some embodiments, the controller 20 includes predetermined routines or schedules for operation of the vibration unit. For example, the controller 20 may operate the vibration unit 23 in a constant vibration mode or a pulsed vibration mode. Sometimes, the vibration unit 23 is turned off, i.e., the vibration unit does not receive power during operation of the breast pump 10, based on a user selection.

Before, during, or after operation of the vacuum pump assembly 22, the controller 20 is configured to operate the heater 25 to deliver heat to the breast. For example, the controller 20 controls the current that is provided to the heater 25 to cause the heating elements 64 to heat to a temperature that is therapeutic for the breast. The controller 20 can operate the heater 25 in coordination with the pump stages of the vacuum pump assembly 22 and/or based on user input. For example, the controller 20 can operate the heater 25 before or during the stimulating mode and/or the operating mode of the vacuum pump assembly 22. Alternatively or additionally, the controller 20 can operate the heater 25 based on a user selection of a heating mode or temperature that is input by the user via the user interface 18. In some embodiments, the controller 20 includes predetermined routines or schedules for operation of the heater 25. For example, the controller 20 may operate the heater 25 to heat the heating elements 64 to a desired temperature and then maintain the temperature. Alternatively, the controller 20 may operate the heater 25 to oscillate between different temperatures. Sometimes, the heater 25 is turned off, i.e., the heater does not receive power during operation of the breast pump 10, based on a user selection. In some embodiments, the heating elements 64 may be heated to a temperature that heats the breast to a temperature in a range of 70° Fahrenheit (F.) to 120° F. or in a range of 80° F. to 110° F. The heating elements 64 are heated to a temperature greater than the desired temperature of the breast to accommodate insulating material between the heating elements 64 and the breast.

The controller 20 may also output information to the nursing woman using the breast pump 10. The information may be displayed on the user interface 18, and/or transmitted using the communications interface 28 to the remote device 33 for display on the device. The information output to the woman may include a notification of which operating mode is being used, a vibration setting, a heat setting, a notification of the detection of letdown, the amount milk in the container 16, the rate of flow of milk into the container 16, the estimated amount of time remaining until the container 16 is full, a notification that the container 16 is full, and/or any other suitable information.

The breast pump 10 may be provided in a pair of breast pumps. For example, the pair of breast pumps 10 may include a first breast pump 10 including a first cup assembly 14 arranged to engage a first breast and a second breast pump 10 including a second cup assembly 14 arranged to engage a second breast. The first and second cup breast pumps 10 may be identical and be configured to operate independently. For example, the breast pumps 10 may include multiple housings 12, controllers 20, pump assemblies 22, vibration units 23, heaters 25, and any other components that correspond to the first and second breast pumps.

Figure 3:
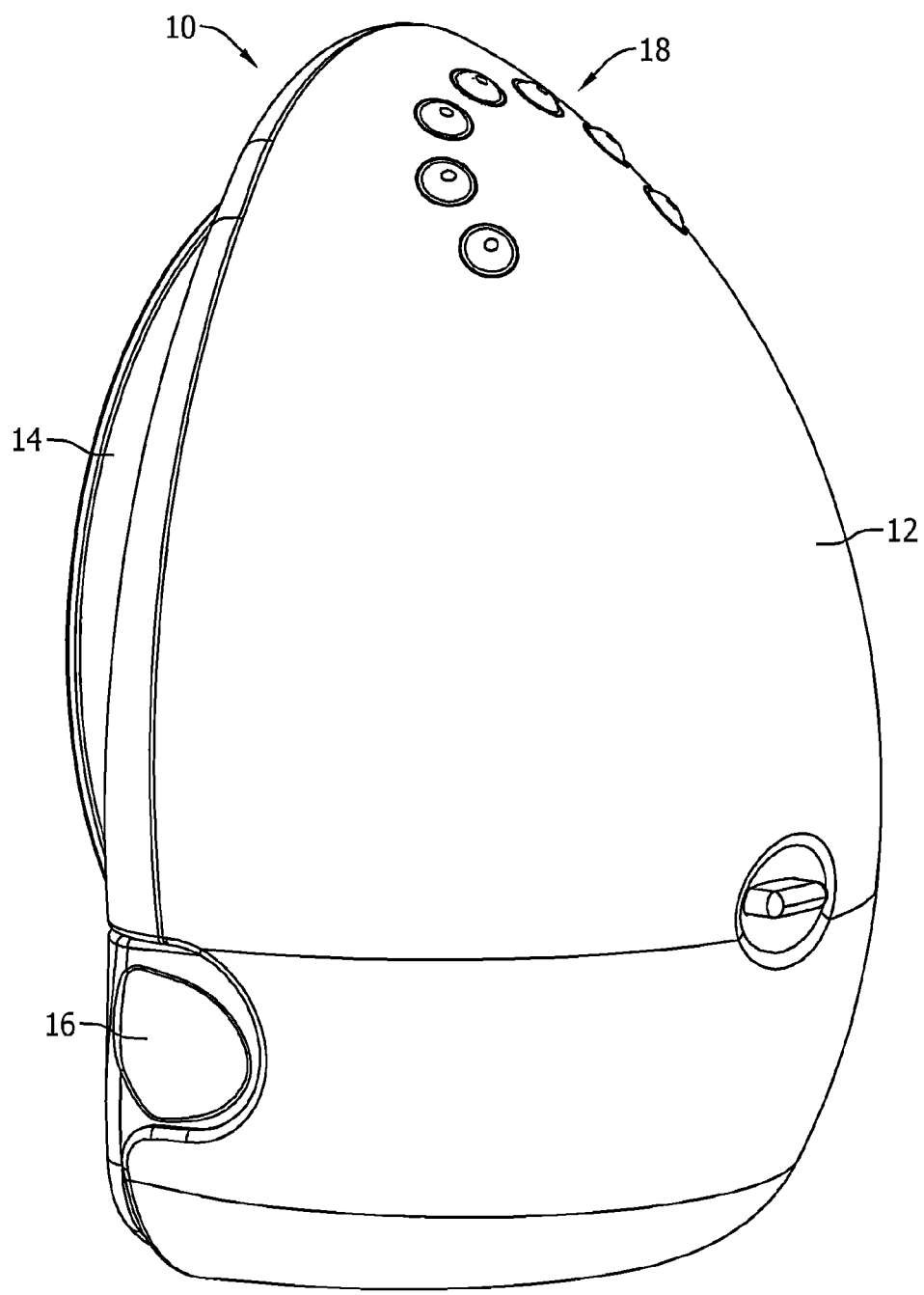
FIG. 3 is a front perspective of the breast pump.
Figure 4:
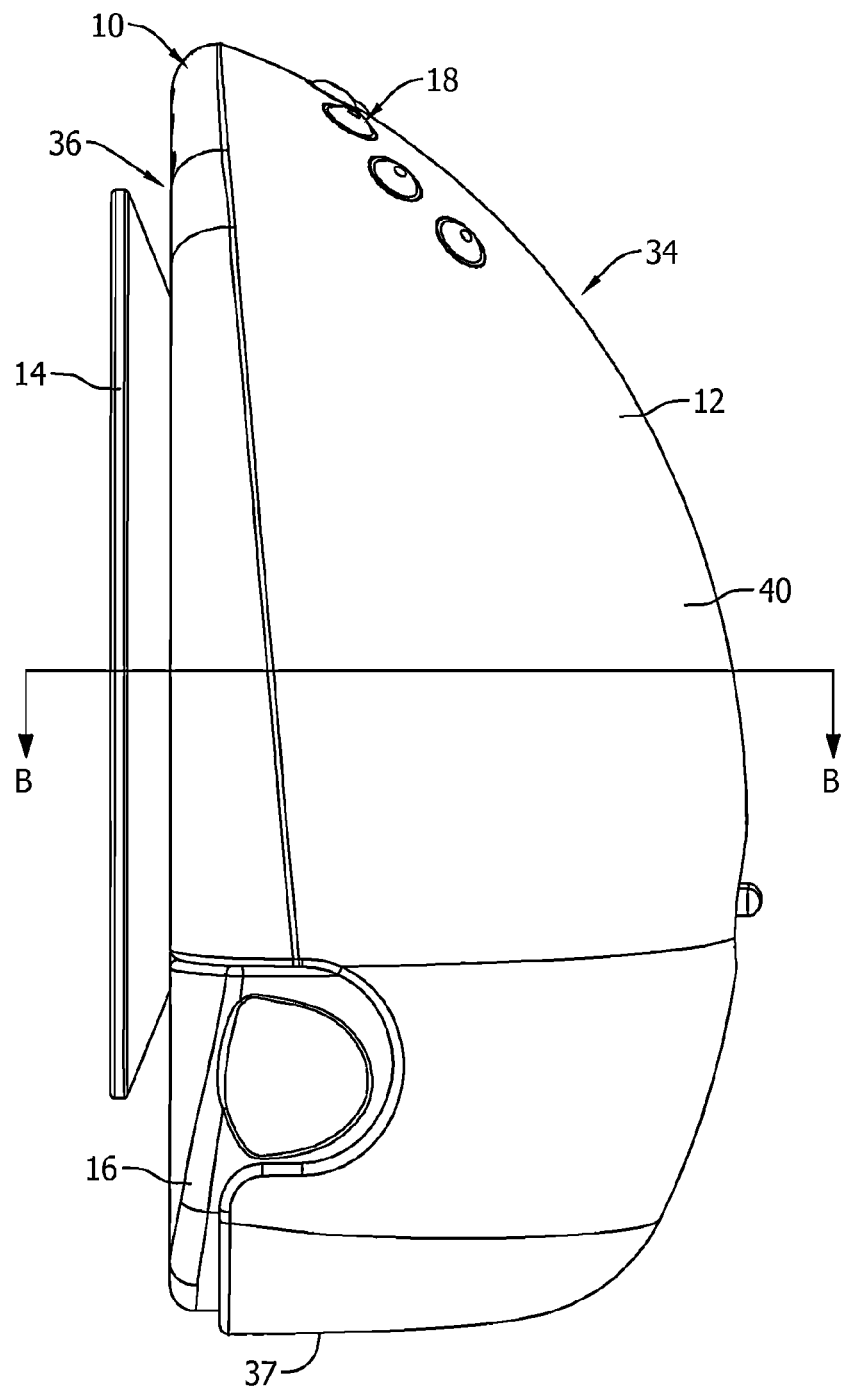
FIG. 4 is a left side view of the breast pump.
Figure 5:
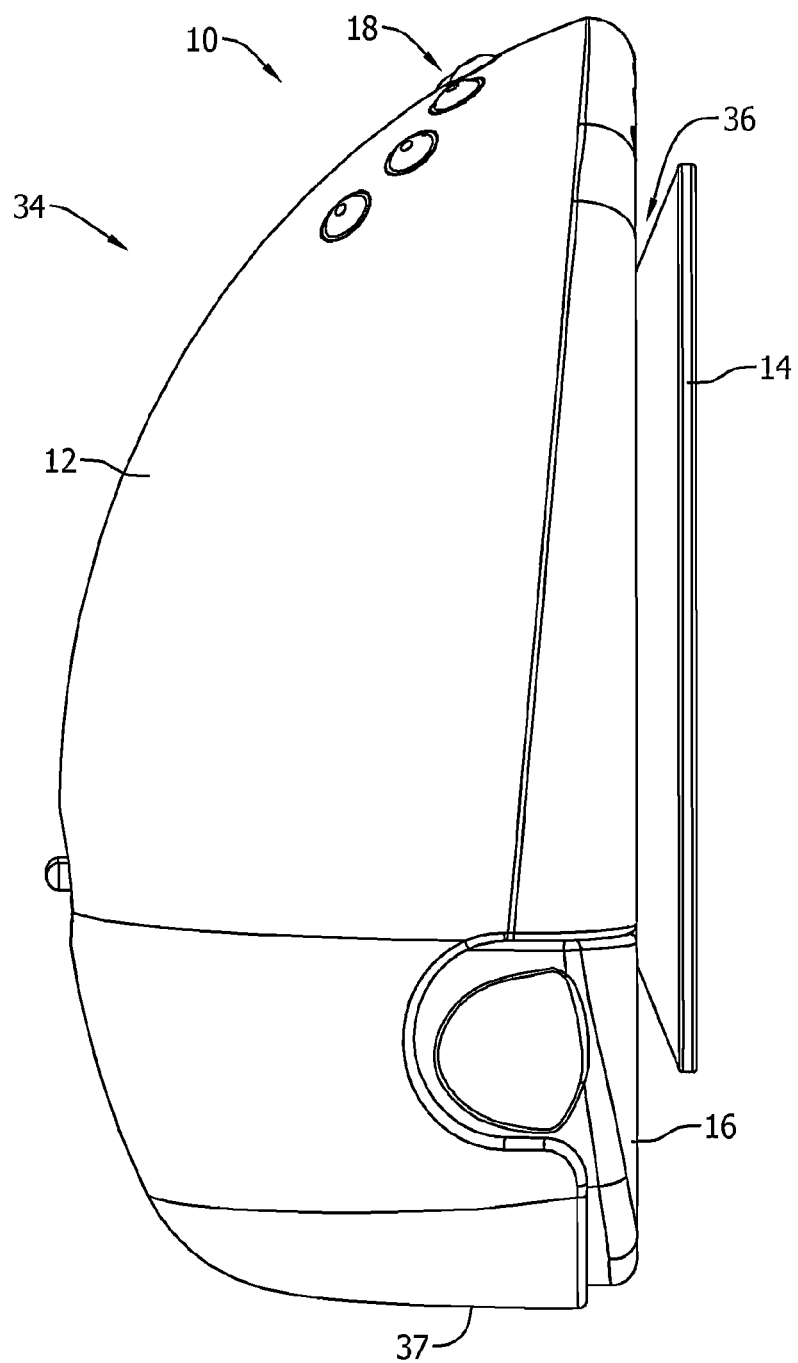
FIG. 5 is a right side view of the breast pump.
Figure 6:
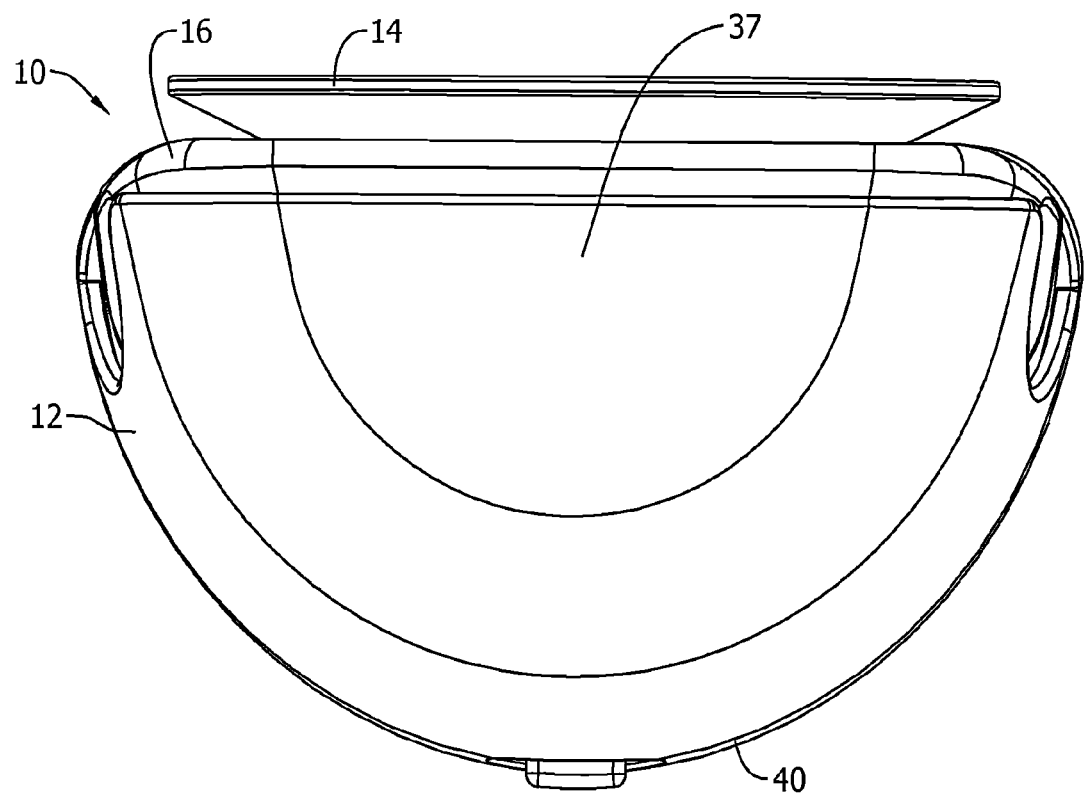
FIG. 6 is a bottom view of the breast pump.

Referring to FIGS. 1-3, in use, the breast pump 10 is inserted within a brassiere or support garment (e.g., the brassiere 100 shown in FIG. 19) and engaged with the breast. For example, the woman may use a pair of the breast pumps 10 and insert one of the breast pumps 10 into each cup of the brassiere. Each breast pump 10 is activated using the user interface 18 to initiate a pumping session. The controller 20 operates the vacuum pump assembly 22 in the stimulating mode, the operating mode, or another mode selected by the user to facilitate the expression of milk from the breasts.

In addition, the controller 20 may operate the vibration unit 23 to provide vibrations to the breast before, during, or after the pumping session. For example, the user may select a vibration setting via the user interface 18. In some embodiments, the controller 20 automatically operates the vibration unit 23 in coordination with the operating modes of the vacuum pump assembly 22.

Also, the controller 20 may operate the heater 25 to provide heat to the breast before, during, or after the pumping session. For example, the user may select a heat setting via the user interface 18. In some embodiments, the controller 20 automatically operates the heater 25 in coordination with the operating modes of the vacuum pump assembly 22.

During operation of the vacuum pump assembly 22, milk collects in the container 16. The breast pump 10 may be operated until the container 16 is full or until a pumping session is complete. The controller deactivates the vacuum pump assembly 22 when the container is full, a preset time is reached, and/or the user deactivates the vacuum pump assembly 22 via the user interface 18 to end a pumping session. The controller 20 may operate the vibration unit 23 and/or the heater 25 after deactivation of the vacuum pump assembly 22 to provide vibration and/or heat treatment to the breasts. The user may select the vibration or heat settings and/or activate the vibration unit 23 and the heater 25 via the user interface 18. The controller 20 may operate the vibration unit 23 and/or the heater 25 for a preset time or until the user deactivates the vibration unit 23 and/or the heater 25 via the user interface 18. The user removes the breast pump 10 from the brassiere or support garment when the pumping session, heat treatment, and/or vibration treatment is complete. The user may remove the container 16 from the housing 12 and transfer any milk in the container 16 into an appropriate milk storage container. The breast pump 10 is then washed and/or disinfected and stored for the next pumping, heat treatment, and/or vibration treatment session.

As a result, the breast pump 10 provides a hands-free pumping experience and allows mobility of the wearer during pumping or treatment sessions. Also, the breast pump 10 is quiet to operate and discrete to use because the breast pump 10 is compact and fits comfortably within a brassiere. In addition, the breast pump 10 can be used to provide heat and/or vibration treatment to the breasts. For example, the heat and vibration treatments can provide a therapeutic effect to the breasts and can reduce incidents of clogged milk ducts. Moreover, the heat and vibration treatments can facilitate an increase in milk production.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A breast pump comprising:
    a housing including a first side and a second side opposite the first side, the first side and the second side defining a cavity therebetween, wherein the second side includes a concave surface defining a recess;
    a breast cup for engaging at least a portion of a breast including a nipple and an area surrounding the nipple, the breast cup attached to the second side of the housing and positioned at least partly within the recess defined by the concave surface;
    a vacuum pump assembly for applying a vacuum to the breast cup and at least the nipple of the breast;
    a container fluidly connected to the breast cup for receiving milk expressed from the nipple of the breast;
    a heater mounted within the cavity of the housing such that the housing is disposed between the heater and the breast cup, the heater comprising at least one heating element, wherein the at least one heating element extends along the concave surface and is mounted to the second side of the housing in thermal connection with the breast cup; and
    a power source mounted within the cavity of the housing and connected to the heater, wherein the heater is configured to provide heat to the breast cup when the power source provides electrical current to the at least one heating element,
        wherein the at least one heating element is configured to heat to a temperature and maintain the temperature, and
        wherein the heat generated by the at least one heating element is configured to be transferred to the breast cup through the housing.

2. The breast pump as set forth in claim 1, wherein the first side of the housing includes a convex surface, the housing being sized to fit within a brassiere such that the first side of the housing contacts the brassiere and the second side of the housing is proximate the breast.

3. The breast pump as set forth in claim 1, wherein the at least one heating element is flexible and shaped to extend at least partly around the breast cup.

4. The breast pump as set forth in claim 3, wherein the at least one heating element is a pair of heating elements that are spaced apart and mounted proximate to the breast cup.

5. The breast pump as set forth in claim 1, further comprising a vibration unit that is mounted within the cavity of the housing and connected to the power source, wherein the vibration unit is configured to vibrate at least the breast cup when the power source provides electrical current to the vibration unit.

6. The breast pump as set forth in claim 5, wherein the vibration unit comprises a motor, a rotor, and an eccentric weight connected to the rotor, the eccentric weight causing the housing and thus the breast cup to vibrate when the motor induces rotation of the rotor.

7. A pair of the breast pumps as set forth in claim 1.

8. The breast pump as set forth in claim 1, wherein the vacuum pump assembly is mounted within the cavity of the housing and connected to the power source, and wherein the vacuum pump assembly is configured to apply a vacuum to the breast engaged with the breast cup when the power source provides electrical current to the vacuum pump assembly.

9. The breast pump as set forth in claim 1, wherein the heater further comprises an insulation material positioned on the at least one heating element opposite the breast cup.

10. The breast pump as set forth in claim 9, wherein the insulation material is an insulation sheet positioned on a surface of the at least one heating element opposite the breast cup.

11. The breast pump as set forth in claim 1, wherein the breast cup further comprises a connector that fluidly connects the breast cup to the housing.

12. A breast pump comprising:
    a housing including a first side and a second side opposite the first side, the first side and the second side defining a cavity therebetween;
    a breast cup attached to the housing and shaped to engage at least a portion of a breast including a nipple and an area surrounding the nipple;
    a vacuum pump assembly for applying a vacuum to the breast cup and at least the nipple of the breast;
    a container fluidly connected to the breast cup for receiving milk expressed from the nipple of the breast;
    a vibration unit mounted within the cavity of the housing;
    a heater mounted within the cavity of to the housing such that the housing is disposed between the heater and the breast cup, the heater comprising at least one heating element, wherein the at least one heating element extends along the concave surface and is mounted to the second side of the housing in thermal connection with the breast cup,
        wherein the at least one heating element is configured to heat to a temperature and maintain the temperature, and
    wherein the heat generated by the at least one heating element is configured to be transferred to the breast cup through the housing; and
    a power source mounted within the cavity of the housing and connected to the vibration unit and the heater, wherein the vibration unit is configured to vibrate at least the breast cup when the power source provides electrical current to the vibration unit, and wherein the heater is configured to provide heat to the breast cup when the power source provides electrical current the at least one heating element.

13. The breast pump as set forth in claim 12, wherein the first side of the housing includes a convex surface and the second side of the housing includes a concave surface, the housing being sized to fit within a brassiere such that the first side of the housing contacts the brassiere and the second side of the housing is proximate the breast.

14. The breast pump as set forth in claim 12, wherein the at least one heating element is flexible and shaped to extend at least partly around the breast cup.

15. The breast pump as set forth in claim 12, wherein the at least one heating element is mounted proximate to the breast cup.

16. The breast pump as set forth in claim 12, wherein the vibration unit comprises a motor, a rotor, and an eccentric weight connected to the rotor, wherein the eccentric weight causes the housing and thus the breast cup to vibrate when the motor induces rotation of the rotor.

17. A pair of the breast pumps as set forth in claim 12.

18. The breast pump as set forth in claim 12, wherein the vacuum pump assembly is mounted within the cavity of the housing and connected to the power source, and wherein the vacuum pump assembly is configured to apply a vacuum to the breast engaged with the breast cup when the power source provides electrical current to the vacuum pump assembly.

\* \* \* \* \*